United States Patent [19]

Chu

[11] Patent Number: 5,199,945
[45] Date of Patent: Apr. 6, 1993

[54] ELECTRO-MOTIVE ENEMA

[76] Inventor: Ven-Chung Chu, 3 Fl. 3, Lane 42, Yu Hsi Street, Yung Ho City, Taipei Hsien, Taiwan

[21] Appl. No.: 555,850

[22] Filed: Jul. 23, 1990

[51] Int. Cl.⁵ .............................................. A61M 3/02
[52] U.S. Cl. .................................... 604/35; 604/262; 604/276
[58] Field of Search .................... 604/35, 27, 45, 73, 604/262, 275, 276, 345

[56] References Cited

U.S. PATENT DOCUMENTS

| | | | |
|---|---|---|---|
| 1,747,391 | 2/1930 | Sarason | 604/262 |
| 2,267,909 | 12/1941 | Grauert | 604/276 |
| 3,028,863 | 4/1962 | Mattson | 604/262 X |
| 3,180,334 | 4/1965 | Glenn | 604/276 |

*Primary Examiner*—William H. Grieb
*Attorney, Agent, or Firm*—Esso International Patent and Trademark Office

[57] ABSTRACT

It is an enema device, in which an electro-motive pump is used for adapting to different water containers, and a power supply unit in the device may be a rectifier or a car power supply; a rubber tube is connected with a rectal pipe or a washing nozzle, which is to be mounted on a stool bag before performing an enema operation.

1 Claim, 6 Drawing Sheets

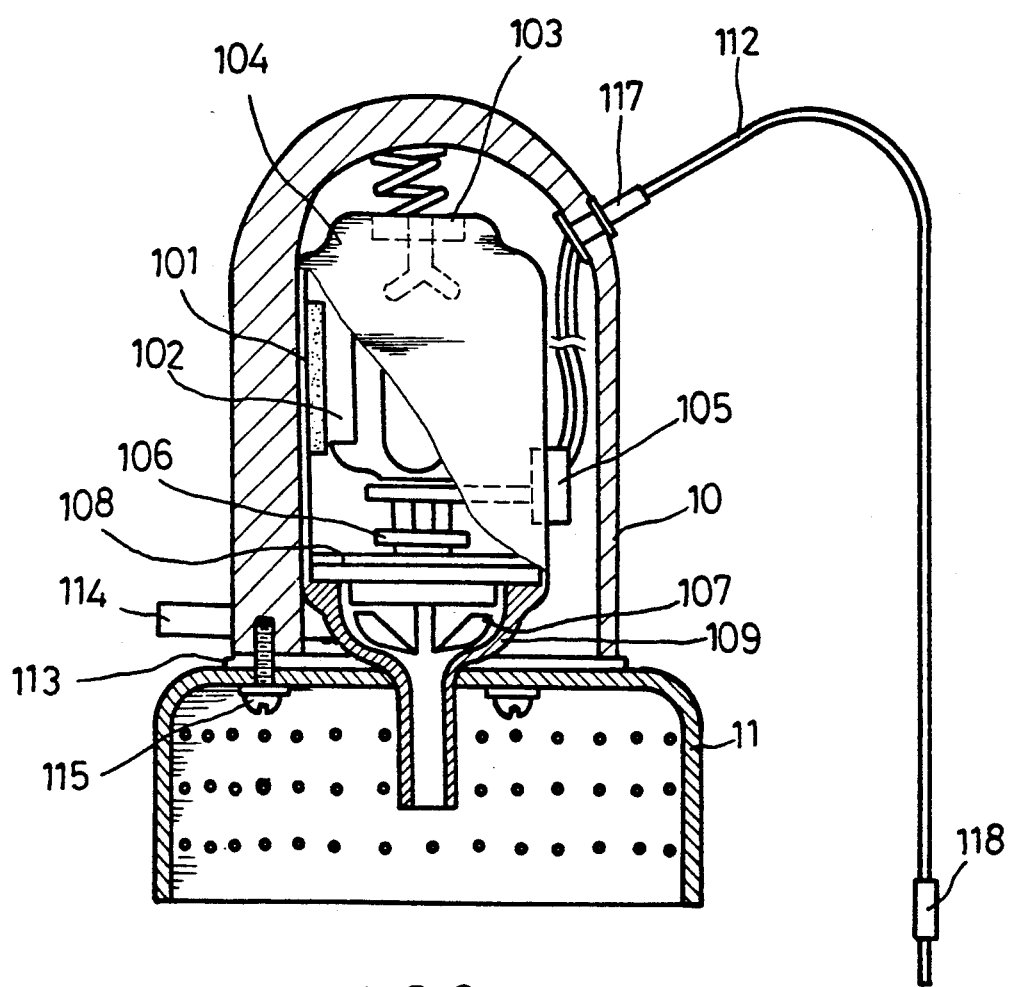
F I G. 2

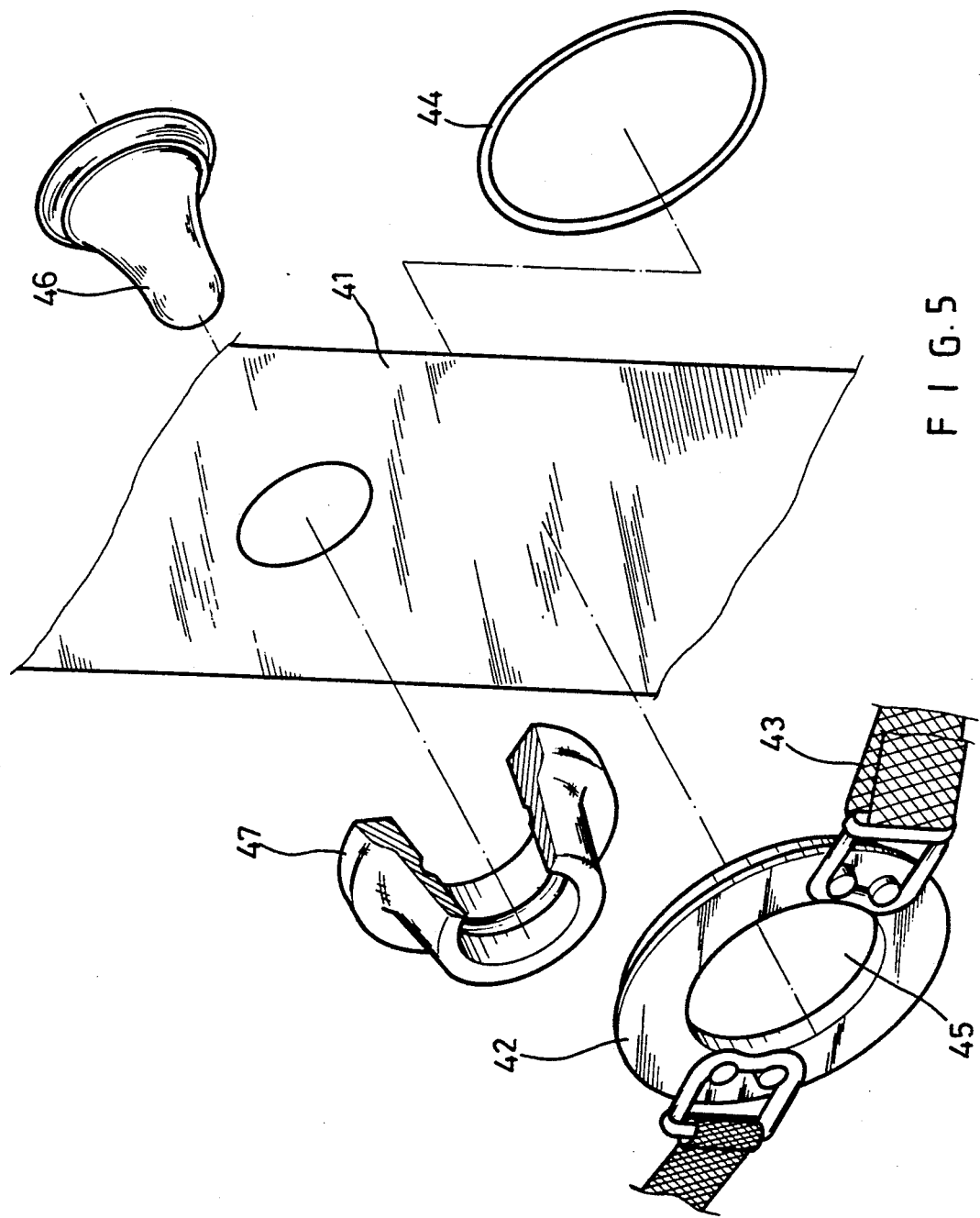

ELECTRO-MOTIVE ENEMA

BACKGROUND OF THE INVENTION

Most of the conventional enema equipment might be classified as an automatic-flowing type, a hand-press type, and a syringe type, among which the automatic-flowing type is deemed the most popular type; however, such a type has to be, in operation, hung on a support and must have a special container; further, as a result of a pressure in the rectum, the washing water is often difficult to flow into the rectum. The hand-press type is considered a reliable type, but it takes time and man-power to operate, and therefore it is merely used as a spore device. The syringe type can not be used by a user himself (or herself); in other words, the aforesaid three types of equipment are unable to meet the requirement of a user on occasions, such as at home, traveling (in a hotel) and camping (or in a car).

SUMMARY OF THE INVENTION

In order to satisfy the general requirements and the requirement of a user who has an artificial anus, the inventor has developed "A D.I.Y. Type of Electro-motive Enema", which comprises an electro-motive pump to be sunk in water; the power supply unit of the present invention can use the commercial A.C. power, a car power supply, a rechargeable battery or a dry battery. Since the pump can be sunk in a water, no special water container is required; since a pressure valve is furnished in the present invention, a bottle or the like may be used as a water container. The present invention also comprises a washing nozzle, it makes the washing work much easy; Moreover, the fixed pad for the artificial anus has been improved by means of rubber and a clamp. A user can operate it without touching the water and stool and without smelling the odour at all; therefore, the present invention is deemed a reliable and sanitary enema device to meet the requirements on all occasions, such as at home, travelling, camping or others.

BRIEF DESCRIPTION OF THE DRAWINGS

FIG. 3-1 is a bottom view of the power supply unit of the present invention.

FIG. 3-2 is a circuit diagram of the power supply unit of the present invention.

FIG. 5 is a disassembled view of the stoal-exhausting assembly according to the present invention.

DETAILED DESCRIPTION

Figure 1:
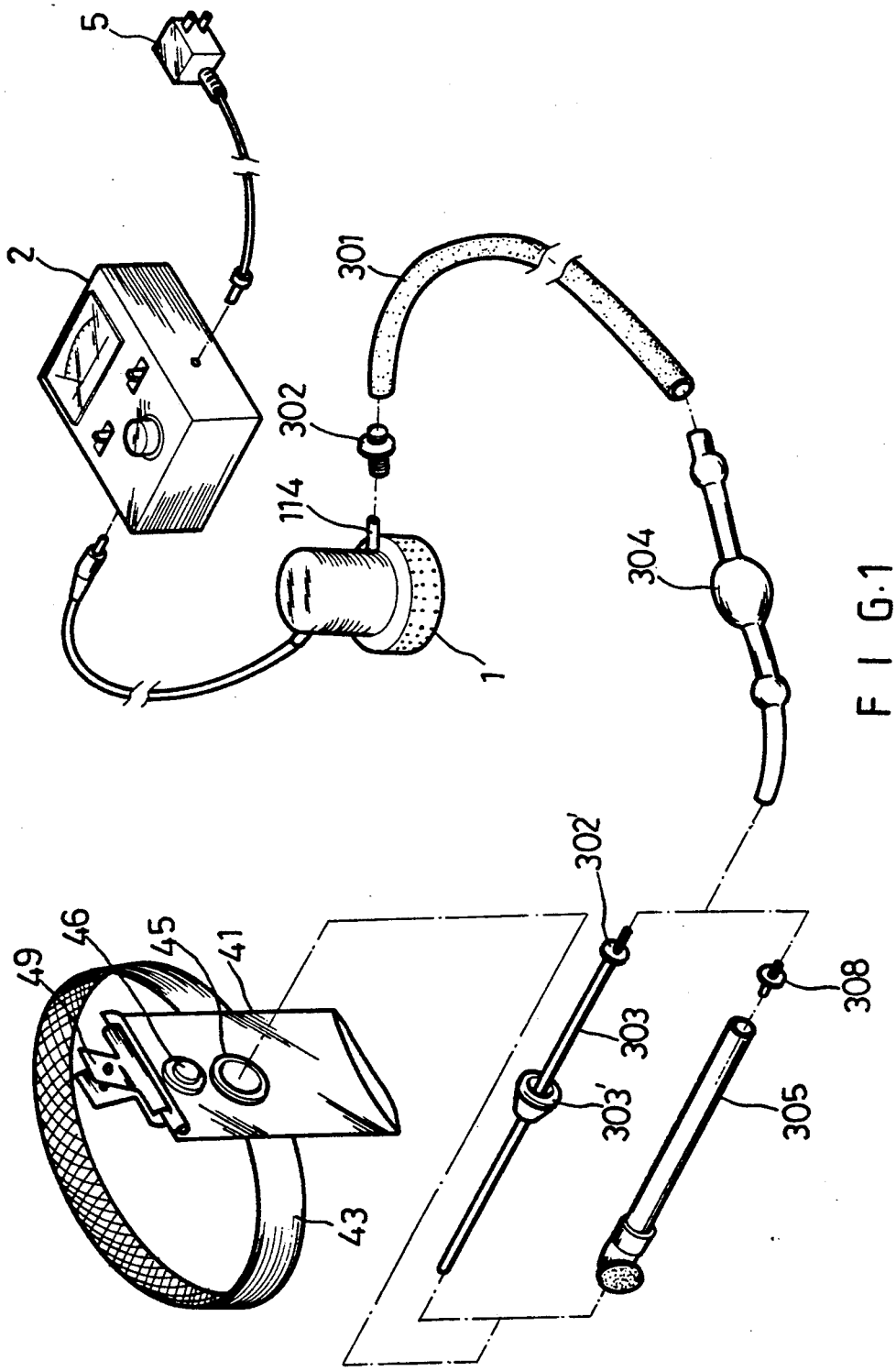
FIG. 1 is a disassembled view of an embodiment according to the present invention.

FIG. 1 is a disassembled view of the present invention, which comprises an electro-motive pump 1, a power supply unit 2, a tube assembly 3, and a stoal-exhausting assembly. As shown in FIG. 2, the elector-motive pump 1 includes water-proof housing 10, a base 11, a magnet ring 101, an armature 102, a bearing 103, an aluminium case 104, a carbon-brush block 105 and a water-proof bearing 106. A pump fin assembly 107 is mounted over the water-proof bearing 106, and then a water-proof ring 108 is mounted on the pump fin assembly 107; finally, an outer case 109 is mounted thereon (the water inlet of the outer case 109 facing downwards). The projected edge of the aluminium ease 104 is closed engaged with the edge of the outer case 109. One end of the wires 112 is mounted in a water-proof sleeve 117 on the water proof housing 10, while the other end of the wires 112 is connected with a plug 118, which is to be inserted in a power supply unit 2. A water-seal pad 113 is mounted between the water-proof housing 10 and the base 11; then, a screw 115 is used to fix the base 11; and the water-seal pad 113 together with the water-proof housing 10. A water tube 114 made of rubber extends out of the housing 10 for conveying water for enema out of the pump.

Figure 3:
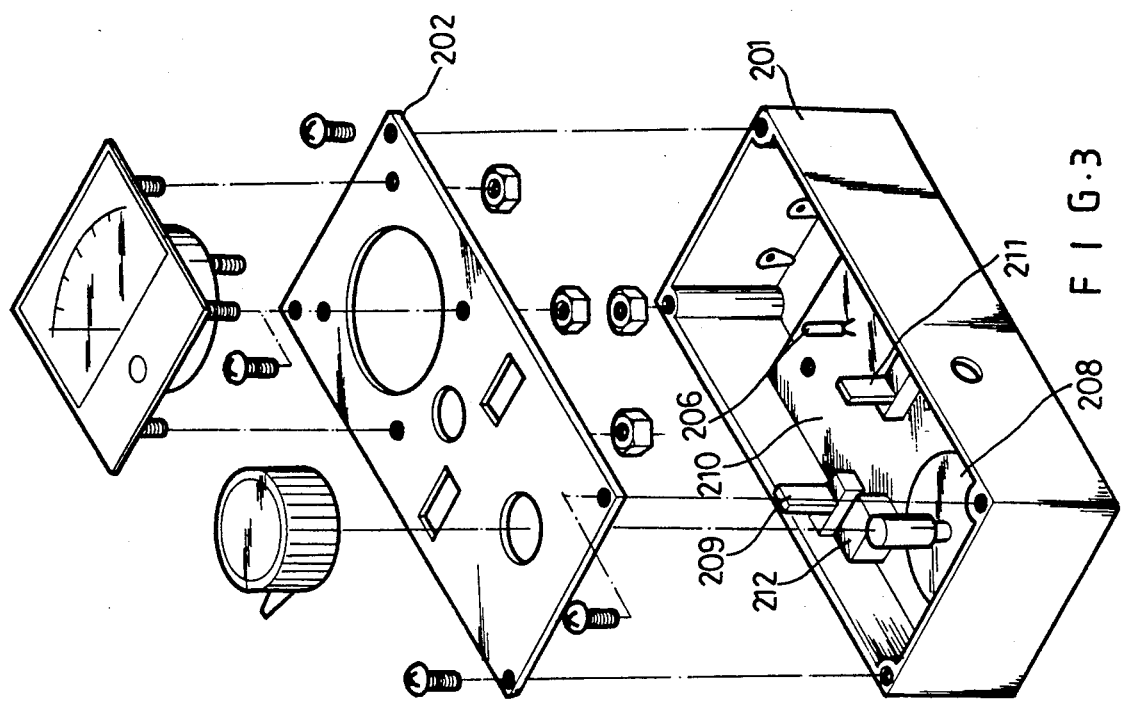
FIG. 3 is a disassembled view of the power supply unit according to the present invention.
Figures 1, 3:
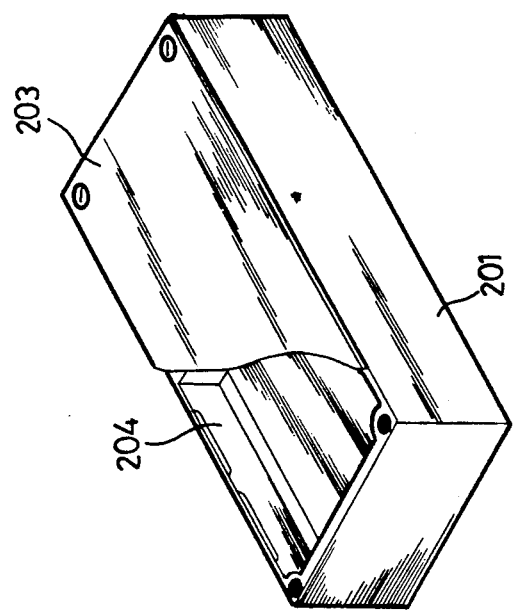
Figures 2, 3:
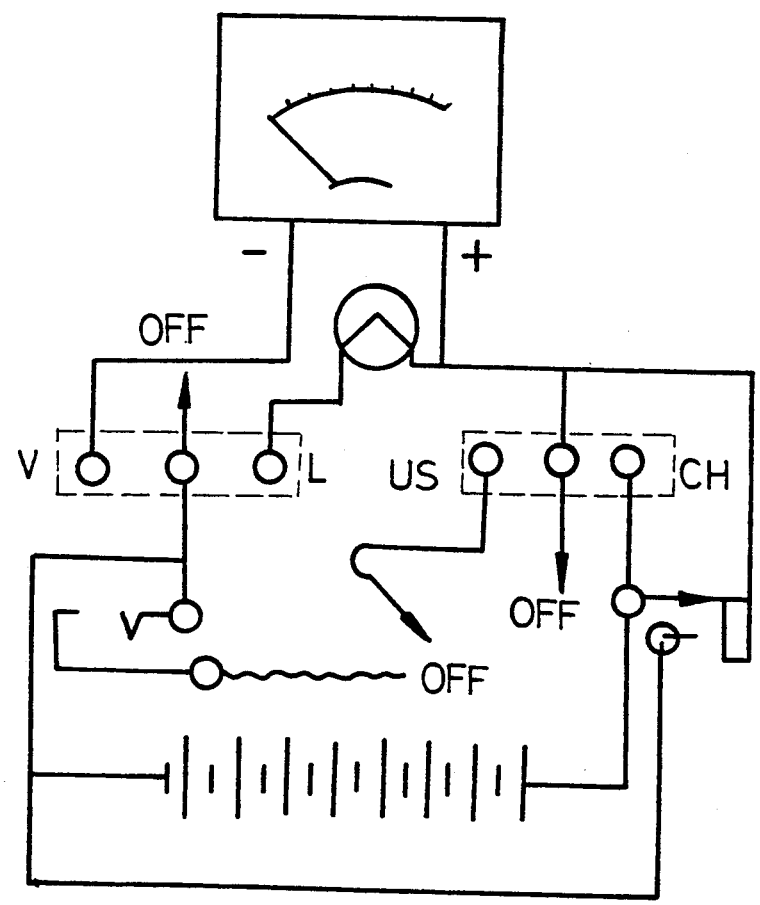
FIG. 2 is a sectional view of the electro-motive pump according to the present invention.

FIG. 3 illustrates a disassembled view of the power supply unit 2 according to the present invention; the power supply unit 2 includes a box body 201, a lid 202, and a bottom plate 203, in which eight dry batteries 204 are loaded as shown in FIG. 3-1, The parts installed inside the box body 201 are a pilot lamp 206, a meter switch 209, a selective switch 207, a circuit board 210 (on which the circuit is shown in FIG. 3-2), a rheostat 208, an input socket 211 and an output socket 212. The minus terminal from the power supply unit, or a rectifier or the car battery will directly be connected to the minus electrode (mid-terminal) of the output socket, while plus terminal of the power supply unit or the like is connected with the mid-terminal of the selective switch through input socket before further being connected with a "US" terminal, a "CH" terminal, the plus electrode of a voltage meter, and one terminal of the pilot lamp. There is a three-pole test switch, of which the mid-terminal is connected with the minus terminal of the power supply, of the voltage meter, and one terminal of the pilot lamp so as to test the condition of the power supply. In "US" circuit, the plus terminal is connected, through the rheostat, with the plus terminal of the output socket so as to adjust the voltage with resistance and to control the rotation speed of the electro-motive pump and the water pressure. There are eight nichrome batteries, of which every two are connected in series; each battery is mounted in the battery box by means of two screws on both ends respectively. The battery can, if necessary, be re-charged with a charge rectifier 5; the battery can also be re-charged with the generator in the car.

Figure 4:
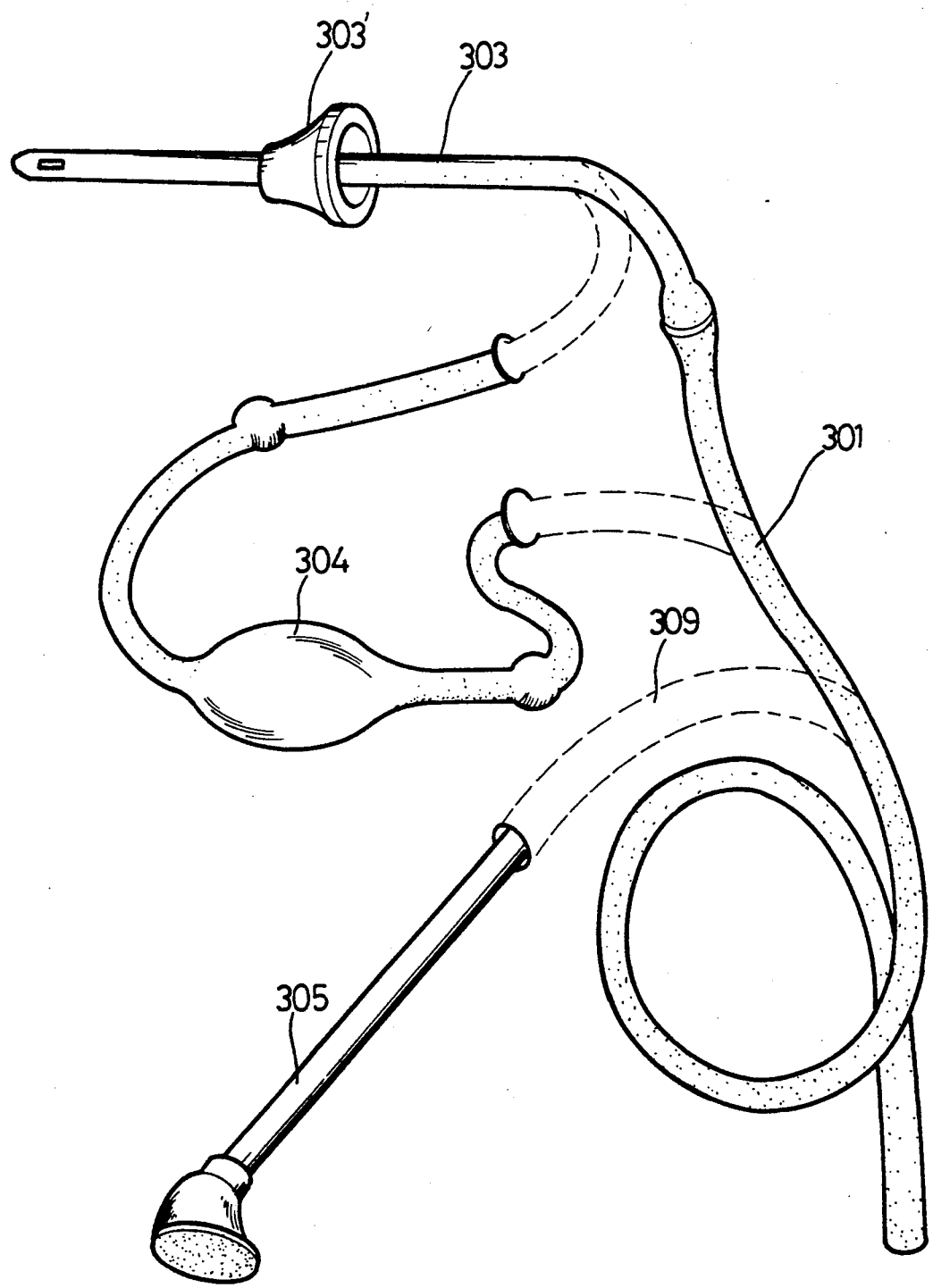
FIG. 4 is a perspective view of the tube assembly of the present invention.

FIG. 4 is a perspective view of the tube assembly 3 of the present invention; one end of thee rubber tube 301 is connected, through a connector 302, with the water tube 114 on the pump, while the other end thereof is connected, through another connector 302', with the syringe tube 303. The rectal pipe 303 is mounted with a sleeve plug 303' for fitting in the anus to prevent water from leaking out. Both ends of the pressure valve 304 are connected with two tubes respectively (in the event of shortage of water, the pressure valve may be connected with a bottle or the like filled with water). One end of the pressure valve is the inlet of water, i.e., a one-way valve, white the other end is the outlet thereof. The washing nozzle 305 may be a hand pipe for inserting into an anus; one end of the washing nozzle 305 is connected with a connector 308, which is then connected with a rubber tube 309.

FIG. 5 illustrates a disassembled view of the stool-exhausting assembly 4, which includes a plastic stool bag 41, a fixed pad 42, an adjustable belt 43 being fixedly attached to the fixed pad 42; the center of the fixed pad 42 has a connecting adapter 45. A rubber washer 44 is mounted under the fixed pad 42. The outer body of another connecting adapter 46 is mounted with an outer connector 47; the connecting adapter 46 is mounted in a small hole 48 in the stool bag 41. After the outer connector 47 is mounted on the connecting adapter 46, press the adapter 46 until the groove thereof being caught in the small hole 48 so as to fix the adapter in the stool bag 41.

To operate the enema of the present invention, fasten the belt 43 to the buckles on both sides of the fixed pad 42; let the fixed pad 42 align with a round hole on the stool bag 41, and then push the rubber washer 44 into the round hole until the same is fixed to the stool bag 41; then, let the small hole on the pad 42 align with the artificial anus, and put the stool bag 41 into a close stool. The opening of the stool bag 41 is closed with a clamp 49; then, the enema operation can be started.

Under normal operation condition have all the parts in the tube assembly 3 connected together; mount the sleeve plug 303' on the rectal pipe 303; put the pump wire into a container of enema water, and insert the into the output socket of the power supply unit 2; set the selective switch 207 of power supply 2 at the "US" position, and then turn the rheostat to start the electro-motive pump 1 so as to let the enema water flow slowly out of the rectal pipe 303; then, insert the pipe 303 into the anus, and seal the anus with the sleeve plug 303' to prevent from leaking water. The water pressure may be adjusted to an extent that the user can bear.

If the present invention is used for a special artificial anus, the connecting adapters 45 and 46 should be mounted on the stool bag 41 first; then, the buckles of the belt 43 are fastened to the left and right lugs of the pad 42 so as to align the artificial anus with the center of the pad 42; remove the washing nozzle 305, and insert the pipe into the small hole in the center of the connecting adapter 45, and then connect the washing nozzle with the pipe; insert the rectal pipe 303 into the artificial anus; insert the sleeve plug 303' into the connecting adapter 46, and use the middle finger and the index-finger to press the sleeve plug 303' in place from the outside of the stool bag 41 for readiness of enema operation. After a suitable quantity of water is syringed into the rectum, turn off the adjusting knob, and release the middle finger and the index-finger to pull out the rectal pipe 303; the water will flow, through the stool bag, into a close stool or other special container. During the operation steps, no waste matter will be contacted with a user's body and the enema equipment so as to maintain a clean and sanitary condition.

I claim:

1. An electro-motive enema comprising:
   an electro-motive pump, which can be used in any container to pump water;
   a power supply unit including a box body, a lid, a bottom plate, a pilot lamp, a switch and a circuit board; and said bottom plate being loaded with a plurality of batteries; and said power supply unit able to be re-charged with a rectifier and the power supply of a car;
   a tube assembly including a rubber tube, of which one end is mounted with a connector and connected with a water tube of said pump, while the other end thereof is mounted with another connector and connected with a rectal pipe; and said rectal pipe being mounted with a sleeve plug for completely sealing an anus to prevent from leaking water;
   a washing nozzle, which can be inserted directly into anus in use;
   a stool-exhausting assembly including a stool bag of which one end is closed with a clamp;
   a fixed pad with a rubber washer;
   a belt being fastened in buckles on both sides of said fixed pad; and
   a connecting adapter being mounted in a small hole of said stool bag; and the center round hole thereof being used for inserting said rectal pipe or a washing nozzle; and said sleeve plug being used for sealing the anus during enema operation.

* * * * *